United States Patent
Denyer et al.

(10) Patent No.: US 6,584,971 B1
(45) Date of Patent: Jul. 1, 2003

(54) DRUG DELIVERY APPARATUS

(75) Inventors: Jonathan Stanley Harold Denyer, Chichester (GB); Anthony Dyche, Hampshire (GB); Ivan Richard Prince, Southhampton (GB)

(73) Assignee: Medic-Aid Limited, Southampton (GB)

( * ) Notice: Subject to any disclaimer, the term of this patent is extended or adjusted under 35 U.S.C. 154(b) by 41 days.

(21) Appl. No.: 09/608,662

(22) Filed: Jun. 30, 2000

Related U.S. Application Data (63) Continuation-in-part of application No. 09/223,824, filed on Jan. 4, 1999, now Pat. No. 6,367,470, which is a continuation-in-part of application No. PCT/GB99/03540, filed on Oct. 26, 1999.

(51) Int. Cl.[7] ............................................. A61M 16/00
(52) U.S. Cl. ........................... 128/203.14; 128/203.12; 128/203.23; 128/203.24
(58) Field of Search ........................ 128/200.14–200.24, 128/203.12, 203.14, 203.23, 203.24, 203.25

(56) References Cited

U.S. PATENT DOCUMENTS

| | | |
|---|---|---|
| 3,741,208 A | 6/1973 | Jonsson et al. |
| 4,533,082 A | 8/1985 | Maehara et al. |
| 4,819,629 A | 4/1989 | Jonson |
| 4,832,012 A | 5/1989 | Raabe et al. ........... 128/200.21 |
| 5,261,601 A | 11/1993 | Ross et al. |
| 5,549,106 A | 8/1996 | Gruenke et al. |
| 5,584,468 A | 12/1996 | Meglino et al. |
| 5,694,920 A | 12/1997 | Abrams et al. ......... 128/200.16 |
| 5,823,179 A | 10/1998 | Grychowski et al. ... 128/100.18 |
| 5,826,570 A * | 10/1998 | Goodman et al. ..... 128/200.14 |
| 6,116,233 A | 9/2000 | Denyer et al. ......... 128/200.18 |
| 6,192,876 B1 * | 2/2001 | Denyer et al. ......... 128/205.25 |

FOREIGN PATENT DOCUMENTS

| | | |
|---|---|---|
| EP | 0 667 168 | 2/1994 |
| EP | 9627266 A2 | 12/1994 |
| GB | 2 077 444 | 6/1981 |
| GB | 2 294 402 | 10/1995 |
| WO | WO94/07607 | 4/1994 |
| WO | WO96/13292 | 5/1996 |
| WO | WO 97/48431 | 6/1997 |
| WO | WO97/29851 | 8/1997 |
| WO | WO97/48431 | 12/1997 |

OTHER PUBLICATIONS

Jonathan Stanley Harold Denyer, et al., "Breathing Patterns In Adult Patients" ISAM FOCUS SYMPOSIUM: Aerosol Therapy With Small Volume Nebulizers: Laboratory To Bedside; Sep. 4–5, 1996, Tours, France.

ISAM Focus Symposium: Aerosol Therapy with Small Volume Nebulizers: Laboratory To Bedside; "*Breathing patterns In Adult Patients*", Sep. 4–5, 1996, Tours, France.

\* cited by examiner

Primary Examiner—Glenn K. Dawson
(74) Attorney, Agent, or Firm—William A. Simons; Wiggin & Dana (57) ABSTRACT

A nebulizer has structure for determining the duration of a pulse of atomization during inspiration, the determination structure including components for measuring the tidal volume of a patient, measuring the duration of inspiration, for storing estimates of the volume of a patient's upper airway, and for calculating the duration of the pulse. The duration of the pulse is calculated on the basis of the tidal volume, the duration of inspiration, and the stored estimated volume of patient's upper airway.

35 Claims, 10 Drawing Sheets

$$\text{Pulse time} = 50\% \text{ sum } \frac{(T1 + T2 + T3)}{3}$$

$$\text{Dose} = \text{Sum } (P1 + P2 + \ldots)$$

DRUG DELIVERY APPARATUS

CROSS-REFERENCE TO RELATED APPLICATIONS

This patent application: is a continuation-in-part of commonly owned U.S. patent application Ser. No. 09/223,824 entitled "IMPROVEMENTS IN AND RELATING TO NEBULISERS" that was filed on Jan. 4, 1999, now U.S. Pat. No. 6,367,470; is a continuation-in-part of commonly owned International Application PCT/GB99/03540 entitled "IMPROVEMENTS IN AND RELATING TO DRUG DELIVERY APPARATUS" that was filed on Oct. 26, 1999; and claims priority of United Kingdom Patent Application 98/23434.7 entitled "NEBULISER" that was filed on Oct. 26, 1998. The disclosures of the foregoing applications are incorporated by reference in its entirety herein as if set forth at length.

BACKGROUND OF THE INVENTION (1) Field of the Invention

This invention relates to drug delivery apparatus, particularly, but not exclusively, nebulizers and dosimetric spacers.

(2) Description of the Related Art

Many different types of nebulizers are known for delivering medication directly into the lungs of a patient, usually for treatment of respiratory diseases. Nebulizers normally deliver medication in the form of droplets or a dry powder. In most nebulizers, atomization of the medicament into a stream of air occurs continuously, regardless of whether the patient is inspiring or expiring. However, the effect of continuous atomization is that a significant proportion of the medication is lost during expiration.

Commonly known nebulizers are either pneumatically operated from a compressed air source connected to the nebulizer which atomizes the liquid, or are ultrasonic nebulizers which use a piezoelectric crystal to atomize the liquid. More recently, a mesh-type nebulizer has been developed in which the medication is forced through a fine mesh in order to create droplets of the medication. A further type of nebulizer, or inhaler, is one which uses a piezoelectric vibrator together with an electro-static charge plate to fluidize and disperse a dry powder aerosol into an airstream. Such a nebulizer is disclosed in U.S. Pat. No. 5,694,920.

The optimum diameter of medication particles or droplets is about 1–5 microns. If the particles or droplets are bigger than this, they are likely to be impacted in the airway before they reach the lungs, but if they are smaller than one micron, they tend to be carried out of the lungs again on exhalation without sedimenting in the lungs.

Nebulizers and inhalers disperse the small particles of medication into an air stream, or stream of other gas, leading to a patient. References to the air which carries the medication entrained in it include other gases suitable for carrying the medication.

One known nebulizer analyses the pressure changes within the device during the first three breaths to determine an average shape of the breathing pattern. A timed pulse of atomization is commenced when starting subsequent inspirations such that atomization occurs for the first 50% of the inspiration. This is illustrated in FIG. 1 where the breathing pattern and pulse are superimposed. This is effective in reducing the loss of medication during exhalation to about 3%. FIG. 1 shows the breaths in a graph of flow rate against time. When the treatment is commenced, a patient breathes in and out three times through the nebulizer before treatment commences. The first three breaths are measured so that the timed pulse of atomization occurs for 50% of the average time of inhalation. The duration of inhalation is indicated as T1, T2 and T3. These timed periods are averaged, and divided by two in order to determine the pulse length for the next fourth breath where treatment starts. For each subsequent breath, the duration of the pulse of atomization is determined by summing the time period of inhalation of the previous three breaths, dividing by three to obtain an average and dividing by two. The dose administered to the patient is directly proportional to the duration of the pulse of atomization, and so the period of atomization is summed, and the atomizer is switched off, or indicates that the patient should stop once the dose administered to the patient reaches the amount of medication prescribed for that treatment.

Other nebulizers are known in which the timed pulse of atomization is fixed to be other than 50% of the duration of inspiration. However, in these other nebulizers, the pulse length must be set for each patient by the clinician. Many of the nebulizers are, therefore, suitable only for use in a controlled environment, such as a hospital. The setting of the pulse length for each patient means that most nebulizers are not suitable for a patient to use at home.

Reference is made to our co-pending International Patent Publication No. WO 97/48431, the disclosure of which is incorporated by reference herein in its entirety as if set forth at length. FIGS. 2 and 3 of this application show the nebulizer which is disclosed in the above co-pending Patent application. Referring to FIG. 2, a mouthpiece 1 is shown through which a patient inhales in the direction of arrow 2. Below the mouthpiece 1 is a removable atomizing section 3 which, in turn, rests on a base 4.

The base 4 is shown in more detail in FIG. 3. Referring to FIG. 3, the base 4 includes an inlet 5 through which air is supplied under pressure from a compressor (not shown). The pressurized air is led via a tube 6 to a manifold 7 which controls the flow of pressurized air to an air outlet 8 which directs air into the atomizing section 3 shown in FIG. 2. The base 4 also includes a pressure sensor 9 which detects the pressure within the atomizing section 3 via a port 10.

Referring again to FIG. 2, air under pressure passes through the air outlet 8 of the base 4 and is conducted through a tubular post 11 to an atomizer nozzle 12 out of which the air issues under pressure. A deflector 13 is located in the path of the pressurised air issuing from the nozzle 12 so that the pressurized air is deflected laterally so as to pass beneath a baffle 14. The passage of the pressurized air across the top of the tubular post 11 causes medication 15 to be drawn up between the outer surface of the tubular post 11 and the inner surface of a sleeve 16 which surrounds the tubular post 11. The medication 15 is atomized in the stream of air, and carried away in the stream of air below the rim of the baffle 14 and up through the mouthpiece 1 to a patient.

The pressure sensor 9 in the base 4 monitors the breathing pattern of a patient, and on the basis of the breathing pattern, the manifold 7 is controlled to supply pressurized air to the atomizing section 3 only during the first 50% of an inhalation phase.

While a particular type of nebulizer is described above, the present application is suitable for application to any type of nebulizer.

The invention also relates to other drug delivery apparatus, such as spacers in which a dose of a drug in droplet or powder form is released into a spacer chamber or holding chamber from which the patient inhales. These are most appropriate for elderly patients or children who have difficulty in using a multi-dose inhaler or dry powder inhaler, for example, because they have trouble coordinating the release of the drug with the beginning of inhalation, or because their inhalation flow rates are too small. For example, spacers are disclosed in International patent publication number WO 96/13294, the disclosure of which is incorporated by reference herein in its entirety as if set forth at length.

BRIEF SUMMARY OF THE INVENTION

According to a first aspect of the present invention, a drug delivery apparatus comprises a drug delivery device for selectively delivering medication-laden air or air not carrying any medication to a patient for inspiration, wherein medication-laden air is selected to be delivered in pulses; a sensor for monitoring a patient's breathing pattern; and a controller for controlling the said delivery device to deliver the medication in pulses, wherein the length of the pulses, and their proportion of the inspiratory phase of the breathing pattern are varied by the controller depending on the breathing pattern monitored by the sensor.

Preferably, the drug delivery apparatus is a nebulizer in which atomization occurs in pulses. It could, alternatively be a dosimetric spacer in which drug-laden air or gas is released from a holding chamber in pulses.

According to a second aspect of the invention, a method for determining the duration of a pulse during which medication-laden air is delivered to a patient during inspiration comprises:

(i) measuring the tidal volume of a patient;

(ii) measuring the duration of inspiration of a patient;

(iii) storing an estimate of the volume of a patient's upper airway; and (iv) calculating the duration of the pulse on the basis of the measured tidal volume of the patient, the measured duration of inspiration and the stored estimated volume of the patient's upper airway.

In this document, the upper airways of a patient are the mouth and trachea, and where a nebulizer is used, preferably include the volume of the nebulizer chamber.

The determination of the length of pulse enables the proportion of the inhalation time during which atomization occurs to be extended above 50% towards 100%. This will result in the patient receiving their treatment in a shorter time, since it will take fewer breaths to deliver the required dose of medication. However, there is no point in continuing delivering the medication into air which is inhaled by the patient at the end of his or her inspiratory phase (the 'end volume'), since it will remain in the upper airways. The medication which does not go beyond the upper airways will be wasted when the patient exhales.

Thus, the invention according to the first and second aspects enables a pulse to be generated which is longer than 50% but which stops before the end volume of inspiration begins. Another advantage of this invention is that a patient's adherence to the treatment regime will be much improved if the length of treatment is reduced.

In addition, the invention allows automatic optimization of the pulse length without it needing to be set by a clinician. This means that the pulse length will automatically be adapted to each patient on the basis of the patient's breathing pattern at the time the medication is being administered. Thus, a nebulizer or other drug delivery apparatus may be used by the patient outside of the controlled environment of a hospital, and may be used at home. In addition, it is possible for the apparatus to indicate when a dose has been administered without the patient needing to count the number of breaths which he or she has taken.

According to the preferred embodiment, the tidal volume measuring device includes a peak flow detector for measuring a patient's peak flow, and a tidal volume predictor for calculating the tidal volume on the basis of the peak flow measured by the peak flow detector, and the duration of inspiration measured by the timer.

Some or all of the values used in the calculations are mean values derived from a number of earlier measurements of each breathing pattern of the patient. For example, the patient will start inspiration through the apparatus, and the medication will not be delivered during the first three breaths. The first three breaths are analysed by recording the duration of inspiration, and the peak flows during inhalation as are required to determine the duration of a pulse of atomization. Delivery of the medication takes place on the fourth and subsequent breaths, in each case the values in the calculations are derived from a number of earlier measurements of the inspiration phase of a patient, in this case the previous three inspiratory phases.

Preferably, where the apparatus is a nebulizer, the atomization is caused by a stream of gas under pressure passing through the nebulizer and sourced from a gas supply means. This gas is normally air, and the source is preferably a compressor operating together with an accumulator. During atomization, gas from the accumulator is used to atomize the medication, and the compressor generates air under pressure to fill the accumulator.

If a patient's inspiration is very long, the accumulator may be caused to be emptied, thereby disrupting atomization. The atomizer, therefore, preferably includes a limiter for limiting the duration of the pulse so as to maintain the accumulator in a state where it is always under some pressure. In addition, the accumulator may include a valve which, when the accumulator is full, vents gas to atmosphere thereby preventing it from becoming dangerously full. It is often preferable to maintain the compressor in operation all the time and to vent excess air to atmosphere rather than to switch the compressor on and off.

According to a third aspect of the present invention, a drug delivery apparatus comprises a tidal volume predictor for predicting the tidal volume of a patient, including a detector for measuring a patient's peak flow, a timer for measuring the duration of inspiration, and a tidal volume calculator for calculating the tidal volume on the basis of the peak flow from the peak flow detector, and the duration of inspiration measured by the timer.

According to a fourth aspect of the invention, a method of predicting the tidal volume of a patient comprises:

(i) measuring a patient's peak flow;

(ii) measuring the duration of inspiration of a patient; and (iii) calculating the tidal volume on the basis of the measured peak flow, and the measured duration of inspiration of the patient.

Measuring the patient's respiratory volume (tidal volume) has previously involved continually monitoring the patient's inspiratory flow, typically every ten milliseconds. The flow rate is integrated over the duration of inspiration to determine the inspiratory volume. However, the third and fourth aspects of the invention determine the tidal volume of a patient much more simply. This invention reduces the amount of data processing which is required, thereby reducing the cost of the overall nebulizer. The peak flow is much simpler to measure, and can be used more simply in a calculation to determine the tidal volume.

According to a fifth and preferred embodiment, a nebulizer comprises apparatus for determining the duration of a pulse of atomization during inspiration, the apparatus including a tidal volume measuring device for measuring the tidal volume of a patient, a timer for measuring the duration of inspiration, an estimate storage device for storing an estimate of the volume of a patient's upper airway, and a calculator for calculating the duration of the pulse on the basis of the tidal volume measured by the tidal volume measuring device, the duration of inspiration measured by the timer, and the stored estimated volume of a patient's upper airway from the storage device.

BRIEF DESCRIPTION OF THE DRAWINGS

Embodiments of the present invention are described below by way of example, and with reference to the drawings in which.

DETAILED DESCRIPTION

Figure 1:
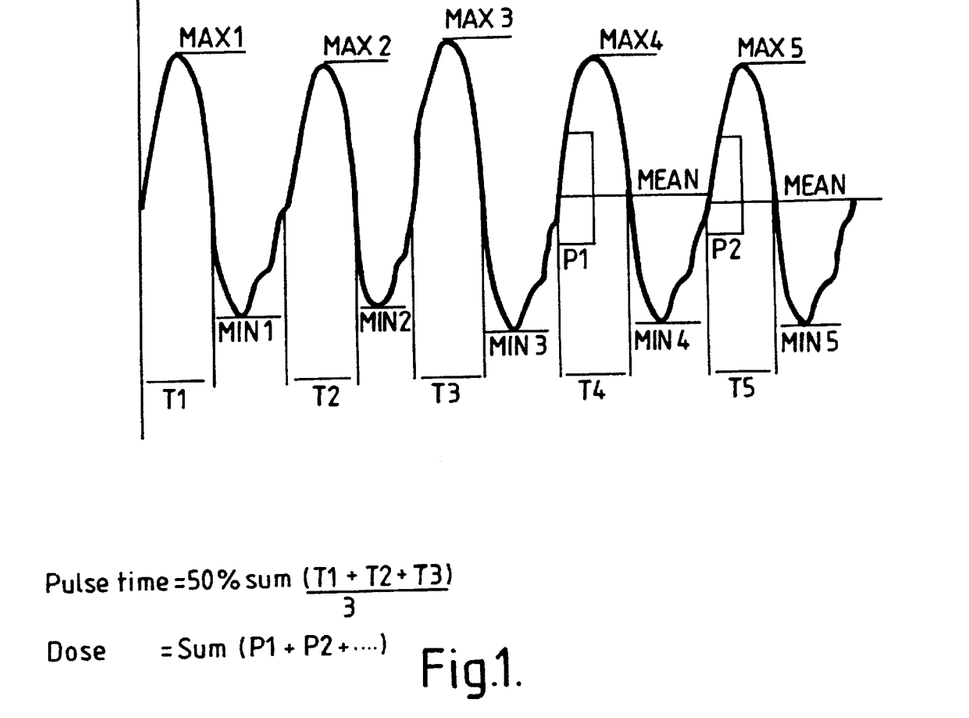
FIG. 1 is a graph showing the inhalation pattern of a patient over time, and indicating when the pulse of atomization occurs in the first 50% of inspiration, as occurs in one known nebulizer.
Figure 2:
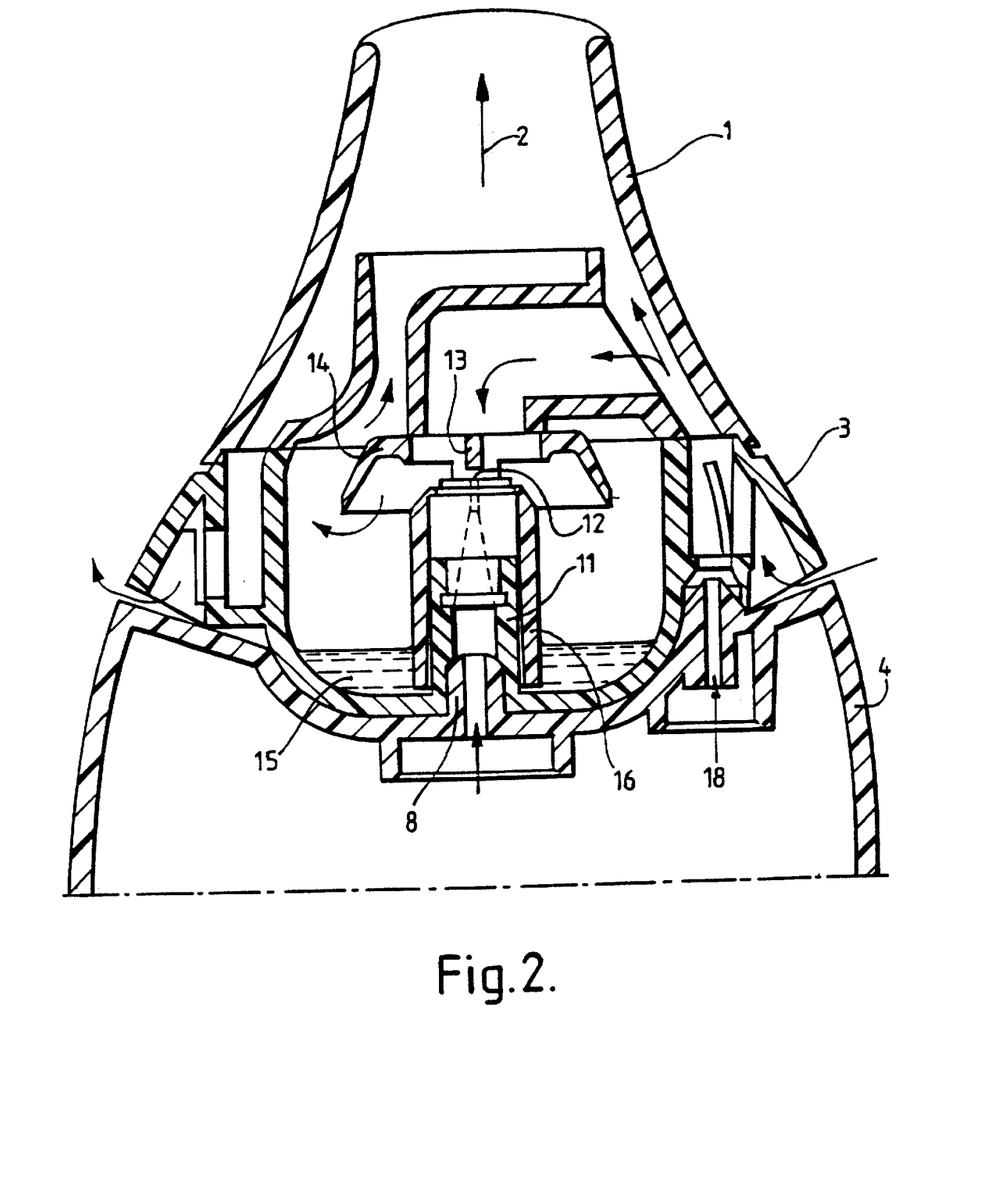
FIGS. 2 and 3 show a known nebulizer which generates pulses of atomization during the first 50% of inspiration.
Figure 3:
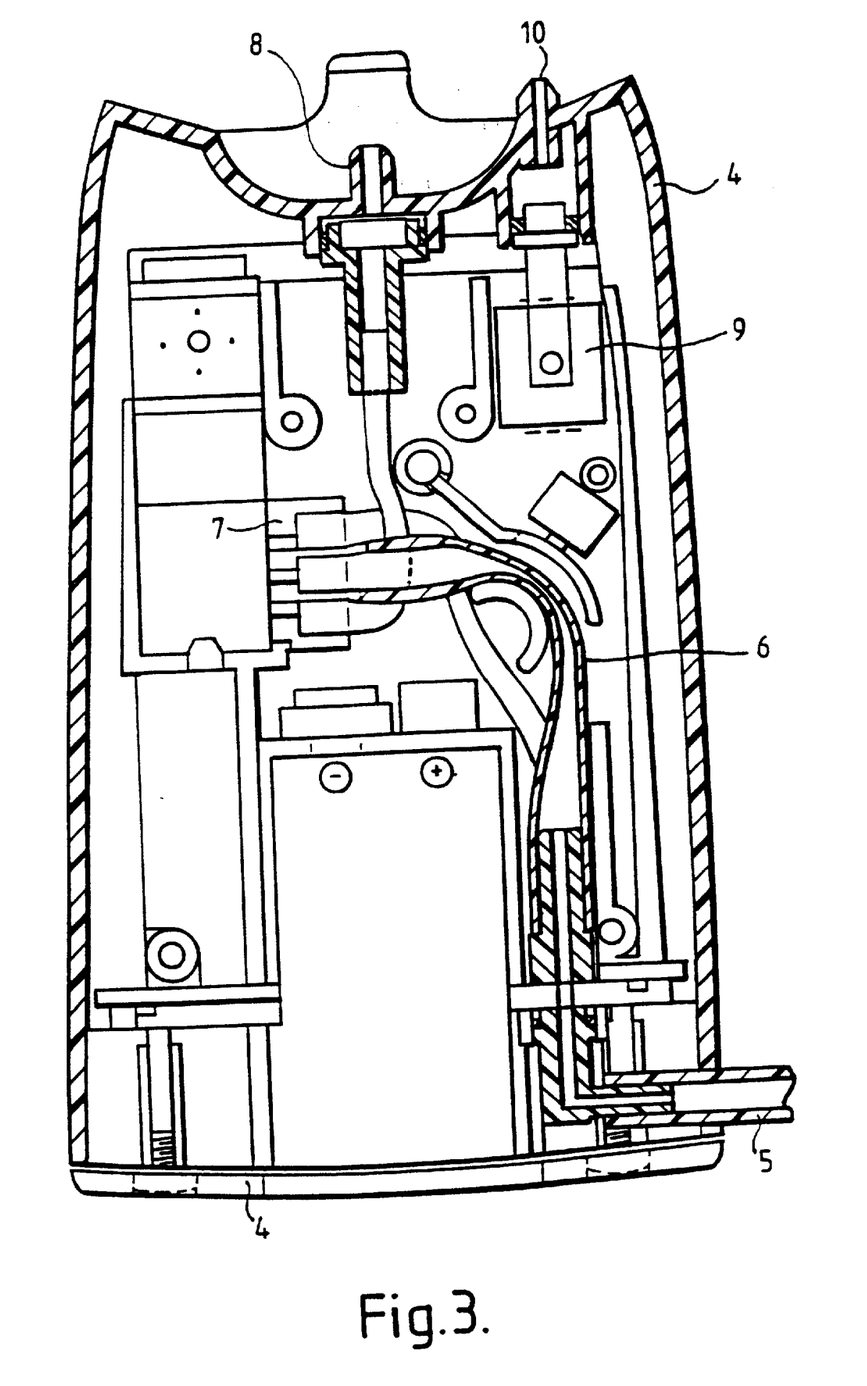

This invention applies, amongst other things, to nebulizers of the type which generate pulses of atomization, as in the prior art nebulizer described above. The invention is not, however, limited to the exact nebulizer described above, but may be applied to other nebulizers. For convenience, the description below of the present invention will refer to components of the prior art device shown in FIGS. 2 and 3, and because many of the components, for example, the manifold, may be used in the present invention. The nebulizer may be one of a jet nebulizer, ultrasonic nebulizer or a pressure mesh nebulizer.

Jet nebulizers are of two kinds, these being air-jet nebulizers and liquid-jet nebulizers. An example of an air-jet nebulizer, which uses a source of compressed air to nebulize a liquid, is disclosed in EP 0627266 (Medic-Aid Limited), the disclosure of which is incorporated by reference herein in its entirety as if set forth at length. An example of a liquid-jet nebulizer, which drives a liquid through one or more nozzle outlets to produce a spray of fine droplets is disclosed in WO 94/07607 (Boehringer Ingelheim International GmbH et al.), the disclosure of which is incorporated by reference herein in its entirety as if set forth at length.

Ultrasonic nebulizers which nebulize a liquid using ultrasonic waves usually developed with an oscillating piezoelectric element, take many forms, these including nebulizers where liquid is in direct contact with the piezoelectric element, where there is an amplifying interface, typically an enclosed fluid, between the piezoelectric element and the liquid, and where the piezoelectric element vibrates a mesh from which an aerosol is generated. Examples of ultrasonic nebulizers are disclosed in U.S. Pat. No. 4,533,082 (Maehara et al.) and U.S. Pat. No. 5,261,601 (Ross et al.), the disclosure of which is incorporated by reference herein in its entirety as if set forth at length. The nebulizers described in those documents include a housing that has a reservoir which holds a quantity of liquid to be dispensed, which housing has a perforated membrane in contact with the reservoir and an ultrasonic vibrator connected to the housing to vibrate the perforated membrane. Another example of an ultrasonic nebulizer is described in WO 97/29851 (Fluid Propulsion Technologies, Inc.), the disclosure of which is incorporated by reference herein in its entirety as if set forth at length. An example of a pressure mesh nebulizer, which may or may not include a piezoelectric element, is disclosed in WO 96/13292 (Aradigm Corporation), the disclosure of which is incorporated by reference herein in its entirety as if set forth at length.

Extending the proportion of the inhalation of the patient in which atomization takes place above 50% results in the patient receiving their treatment faster since it will take fewer breaths to deliver the required volume of medication. However, to avoid waste of the medication which is atomized in the end volume of patient's inspiratory volume, the pulse of atomization must be stopped before the end volume is reached. The end volume is the volume of air inhaled by a patient at the end of the inspiratory volume which remains in the upper airways (the mouth and trachea) and does not enter into the lower parts of the lungs. Medication which is atomized into the end volume is wasted when the patient exhales, together with any air atomized medication left in the nebulizer, since it does not reach the lungs.

The end volume is the volume of the patient's upper airway, and is proportional to the size of the patient. Clearly, the end volume will vary as a percentage of the inspiratory tidal volume since the tidal volume changes significantly depending on the type and extent of the respiratory disease suffered by the patient. The optimum duration of atomization pulse would, therefore, be from the start of inhalation up to the point during inspiration when the volume remaining to be inspired equals the end volume. Atomization would then be stopped and the remaining end volume would clear the atomized medication from the device and the upper airways of the patient and into the lungs. Thus, the percentage of inspiration in which atomized medication is delivered is maximised, thereby minimising treatment time and still avoiding waste of medication. The length of the atomization pulse is dependent upon the patient's inspiratory tidal volume. The nebulizer must therefore measure the patient's tidal volume, preferably on a breath by breath basis so as to calculate, for example from the previous three breaths, an average inhalation volume for the next breath. Thus, the atomization pulse time will be calculated as follows:

Pulse time=(mean inspiratory time)×(mean tidal volume−end volume)÷(mean tidal volume)

Timing means are included in the nebulizer connected to the pressure sensor 9 (shown in FIG. 3) in order to measure the duration of inspiration. Storage means are also included in the nebulizer in which an estimate of the end volume of a particular patient is stored. Since this figure is a constant value for a particular patient, this can be entered at the beginning of a course of treatment, and is estimated on the basis of the size of the patient. The nebulizer includes a means for measuring the tidal volume of a patient. According to one form of the invention, the patient's inspiratory flow is monitored continuously, typically every ten milliseconds, and this is integrated over the inspiratory duration. Another, simpler, way of measuring the tidal volume of a patient is described later in this specification.

The nebulizer also includes means for calculating the atomization pulse time on the basis of the duration of inspiration, the tidal volume and the end volume. The calculation means carries out the calculation outlined above.

In view of the fact that the nebulizer adapts to the breathing pattern of a patient, when the patient starts breathing, no atomization takes place during the first three breaths. Those first three breaths are used to analyse the breathing pattern of the patient. The flow rate of the first three breaths are measured, and from this, the duration of the inhalation phase of the first three breaths are calculated, and an average found. The average duration of inhalation is then used in the calculation to determine the pulse length of atomization during the fourth breath. In addition, as the patient continues to breathe in and out, the previous three breathing patterns are measured and used to calculate the next pulse duration. Thus, if a patient's breathing pattern improves during treatment, the nebulizer will adapt to this change in order to optimize the dose administered during each breath.

Figure 4:
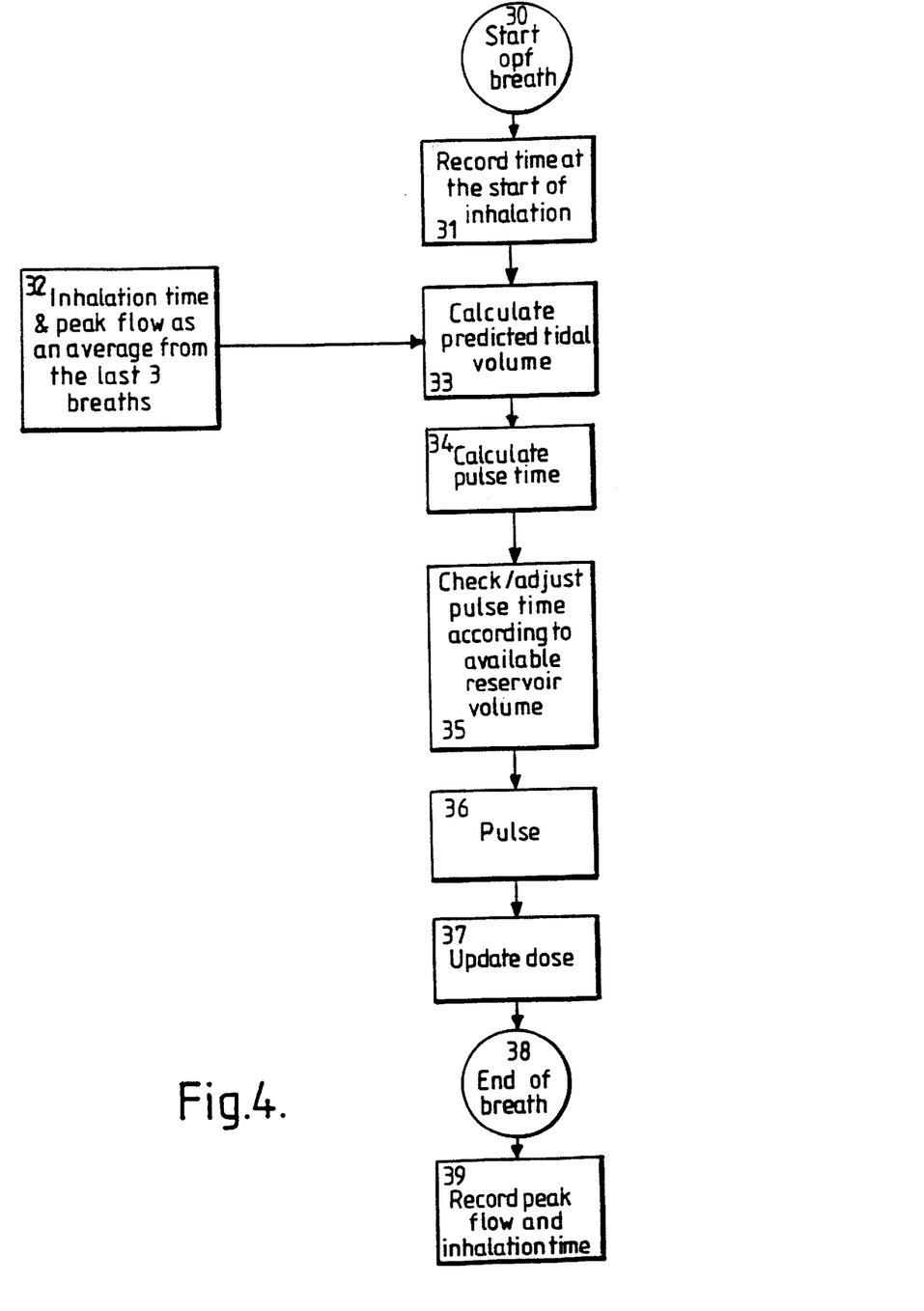
FIG. 4 is a flow diagram showing how the pulse of atomization during inspiration is determined.

Referring now to FIG. 4, the steps taken by the nebulizer and by the patient are described. The first operation, box 30 represents the patient starting to inhale. The timing means records the time at which inhalation starts as shown in box 31, and during inhalation, a calculation is performed to predict the tidal volume of the patient as shown in box 33. This step will be described in more detail later in a specification, but it will be noted that the calculation requires data to be included in the calculation which is the inhalation time and peak flow as an average from the last three breaths, as shown in box 32. The pulse time is then calculated by the calculation means as shown in box 34, and the pulse time is adjusted, as shown in box 35 in the event that the pulse length would exhaust an accumulator from which is pressurised air is supplied to the nebulizer. This step, shown in box 35 is also described in more detail later in this specification. The pulse of atomization occurs during inhalation, and after it has stopped, a calculation is carried out to determine what dose has been atomized. At the end of the breath as shown in box 38, details of the peak flow of the patient inhalation, and the duration of inhalation are recorded so that calculations determining pulse length may be made for subsequent breaths. This is shown in box 39.

Reference is made above to the simpler prediction of tidal volume. As will be appreciated, measuring tidal volume by integrating measured flow rate over the time of inspiration requires considerable processing power and is relatively expensive. A simpler method of determining the tidal volume is proposed which requires much simpler calculations and much simpler measurements to be made for use in such a calculation. To carry out the measurement, the nebulizer includes a peak flow detector for detecting the peak flow rate of inspiration.

The calculated or predicted tidal volume is derived from the peak flow measured by the peak flow detector, and the duration of inspiration measured by the timer. The tidal volume calculation means carries out the following calculation:

Predicted tidal volume=$C \times$Mean Peak Flow$\times$Inspiratory Time$\div 60$ Where C is a constant and it is found that C=0.7.

Figure 5:
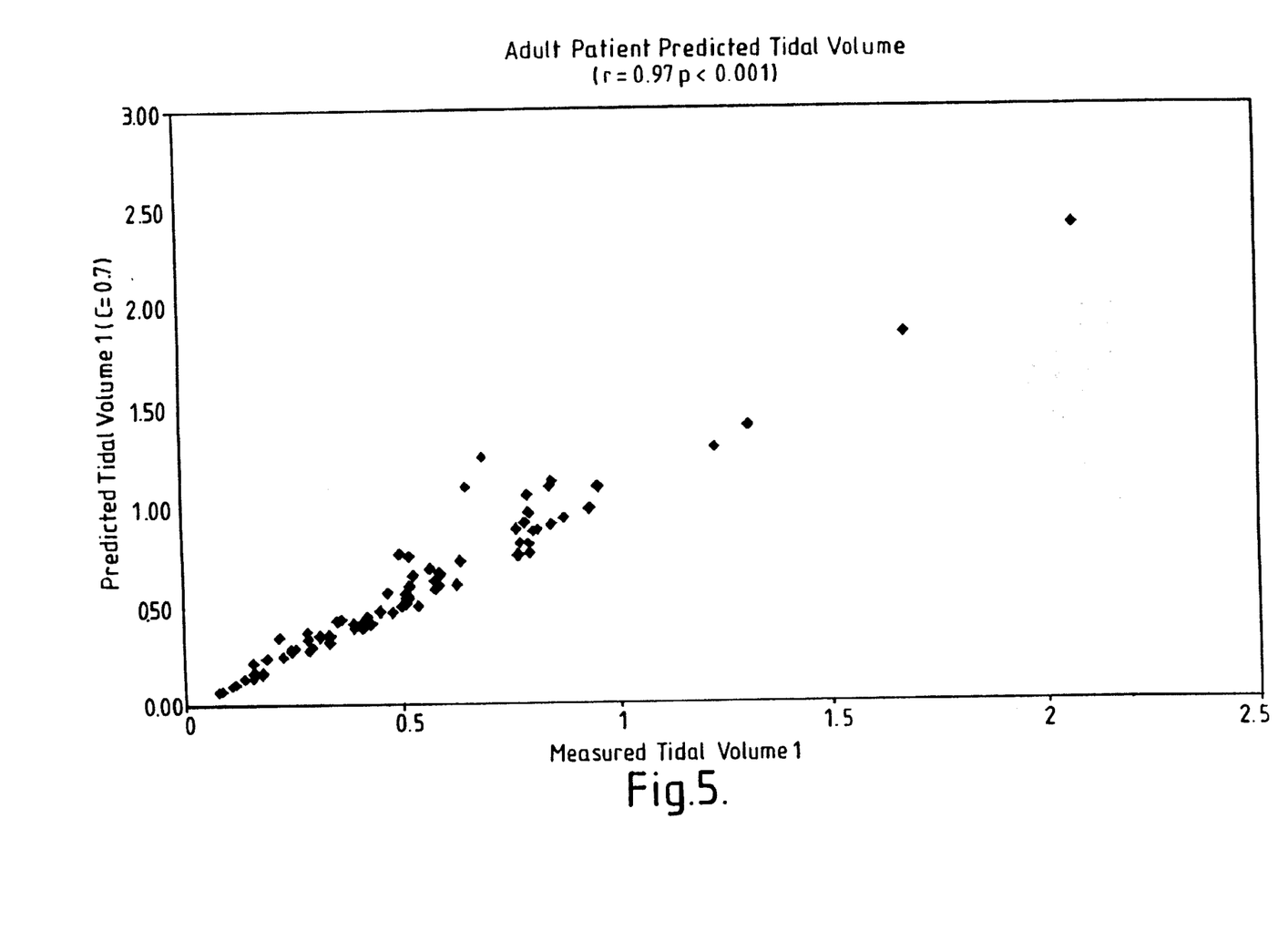
FIG. 5 is a graph showing the predicted tidal volume against measured tidal volume.

FIG. 5 is a graph of the predicted tidal volume against measured tidal volume. Each point on the graph represents a patient whose tidal volume has been measured by a complex tidal volume calculation by integration of the patient's inspiratory flow over the duration of inhalation, and the predicted tidal volume according to the new, simpler method of calculation. It will be seen that the predicted tidal volumes are extremely accurate, and so the predicted tidal volume may be included in the calculation of atomization pulse time.

The use of a low flow rate compressor together with an accumulator to supply compressed air to the nebulizer is disclosed in our earlier Patent application published as WO 97/48431, which is referred to above. In the past, the size of the compressor and accumulator are selected so that the maximum pulse that can be delivered by the device (currently 50% of inspiratory time) does not exceed the accumulator volume for any given pulse or the mean o output of the compressor. Now that the pulse time is variable, it is preferable to calculate the maximum pulse time available from the air supply system. For patients who have a slightly higher inspiratory demand, the pulse time of atomization will be reduced so that the supply capability of the air supply system is not exceeded. The calculations are carried out on a breath by breath basis, assuming that the accumulator is filled at constant flow rate from the compressor. The volume of air added to the accumulator from the end of previous pulse to the start of the next pulse is calculated and then added to the volume remaining at the end of the previous pulse.

Figure 6:
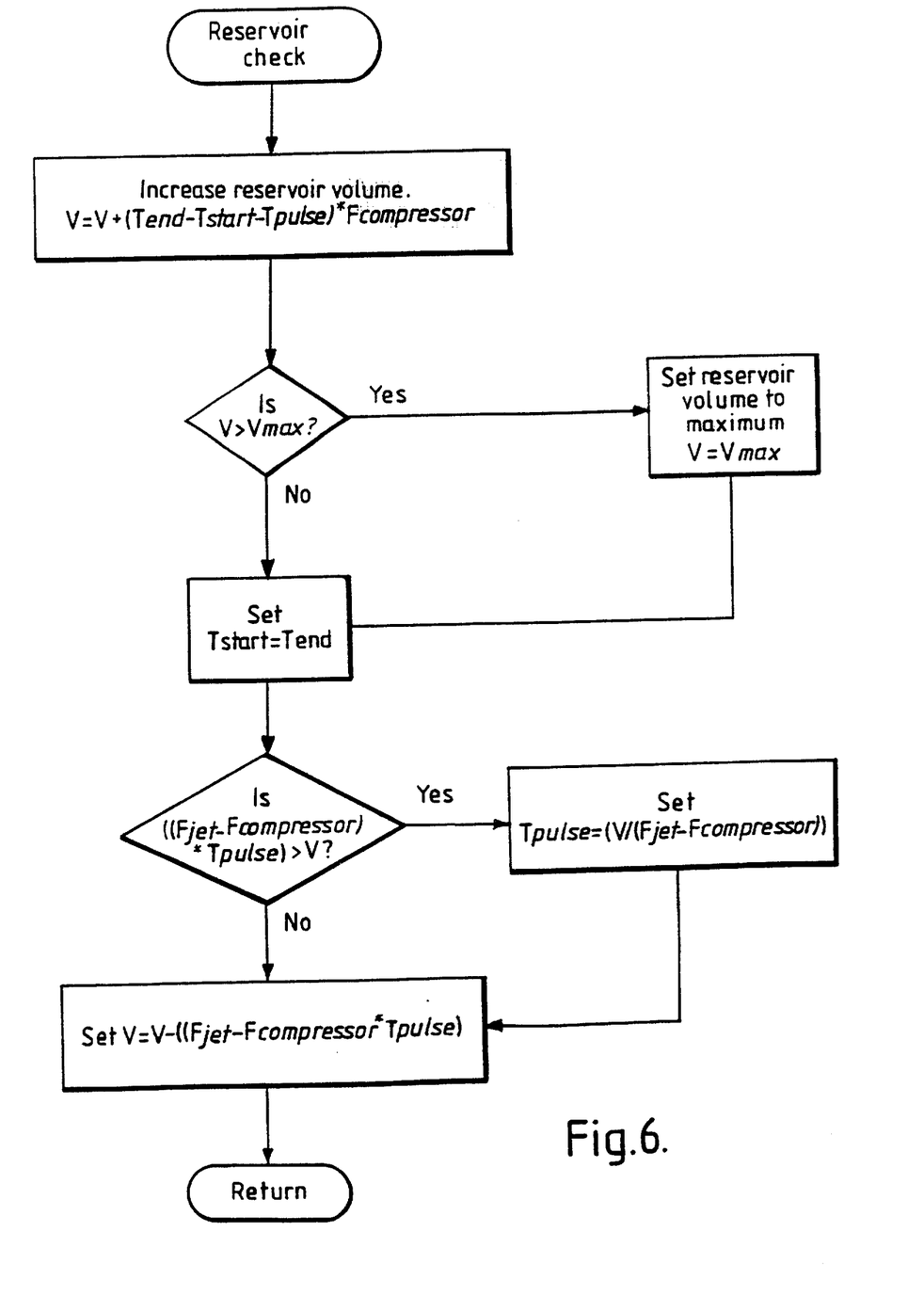
FIG. 6 is a flow diagram showing the limitation of the pulse length depending on the supply of pressurised gas.

FIG. 6 is a flow diagram showing the calculations carried out in ensuring that the volume of air used does not exceed the volume of the accumulator. If the air in the accumulator is calculated to be above the maximum volume of the accumulator, the volume is set to be at its maximum V=$V_{max}$. This is because there is an automatic vent valve which limits the volume of air stored in the accumulator. The maximum pulse time can then be calculated on the basis of the rate of flow of air out of the accumulator which is the flow to the atomizerjet, minus the flow rate to the compressor. If this exceeds the volume available in the accumulator, then the pulse time is limited to the current accumulator volume. The volume of the accumulator at the end of the pulse is then calculated to be used at the beginning of the next calculation occurring at the beginning of the next inhalation of the patient. Thus, the maximum pulse time for individual breaths is calculated without exceeding the capacity of the air supply system. The compressor has a constant output flow rate, typically 1.5 litres per minute and the nebulizerjet has a flow rate of 6 litres per minute during pulsing. The accumulator has a volume of approximately 150 millilitres at NTP.

Figure 7:
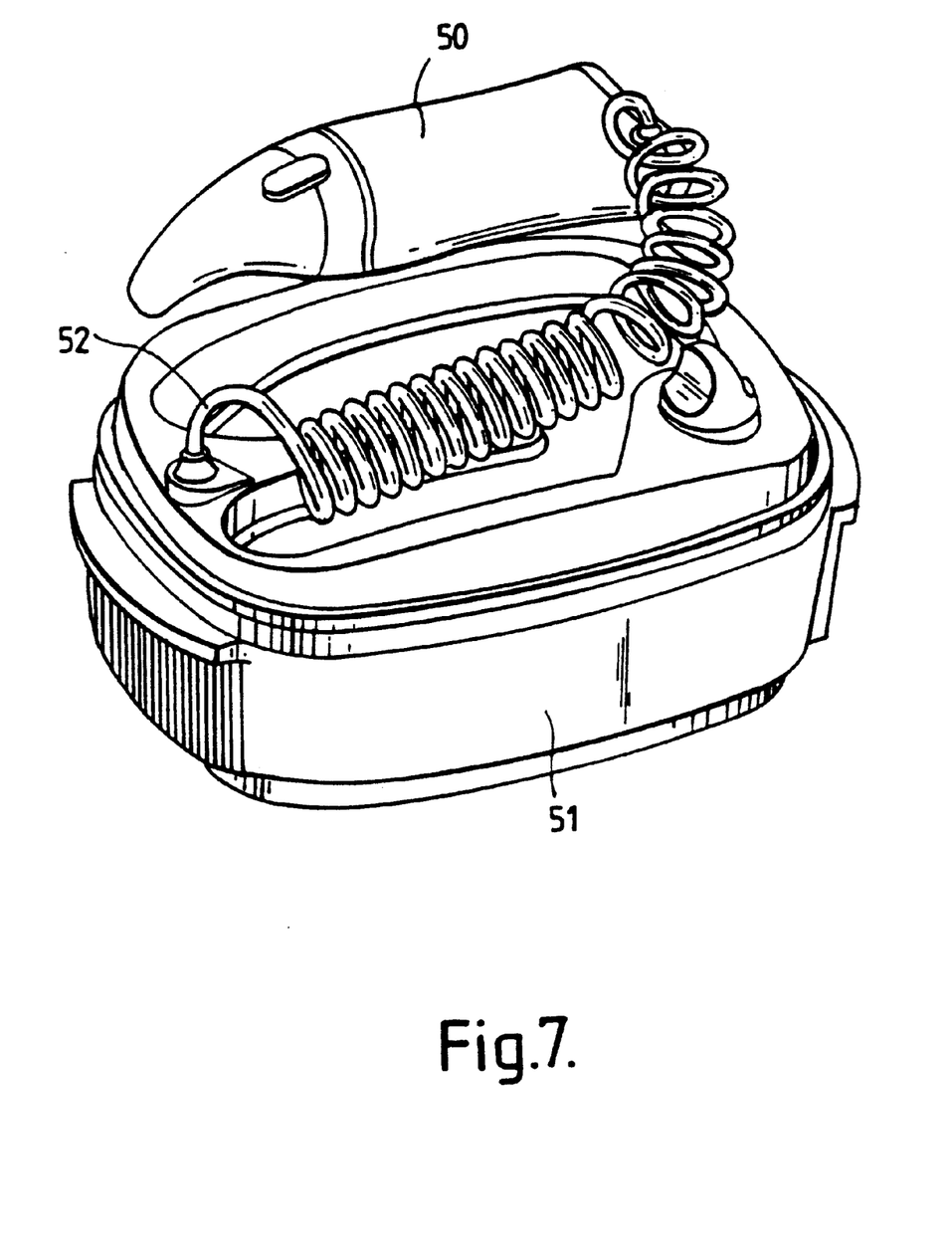
FIG. 7 shows the nebulizer together with a source of pressurised gas.

FIG. 7 shows the nebulizer 50 connected to the air supply 51 by a flexible tube 52.

Figure 8:
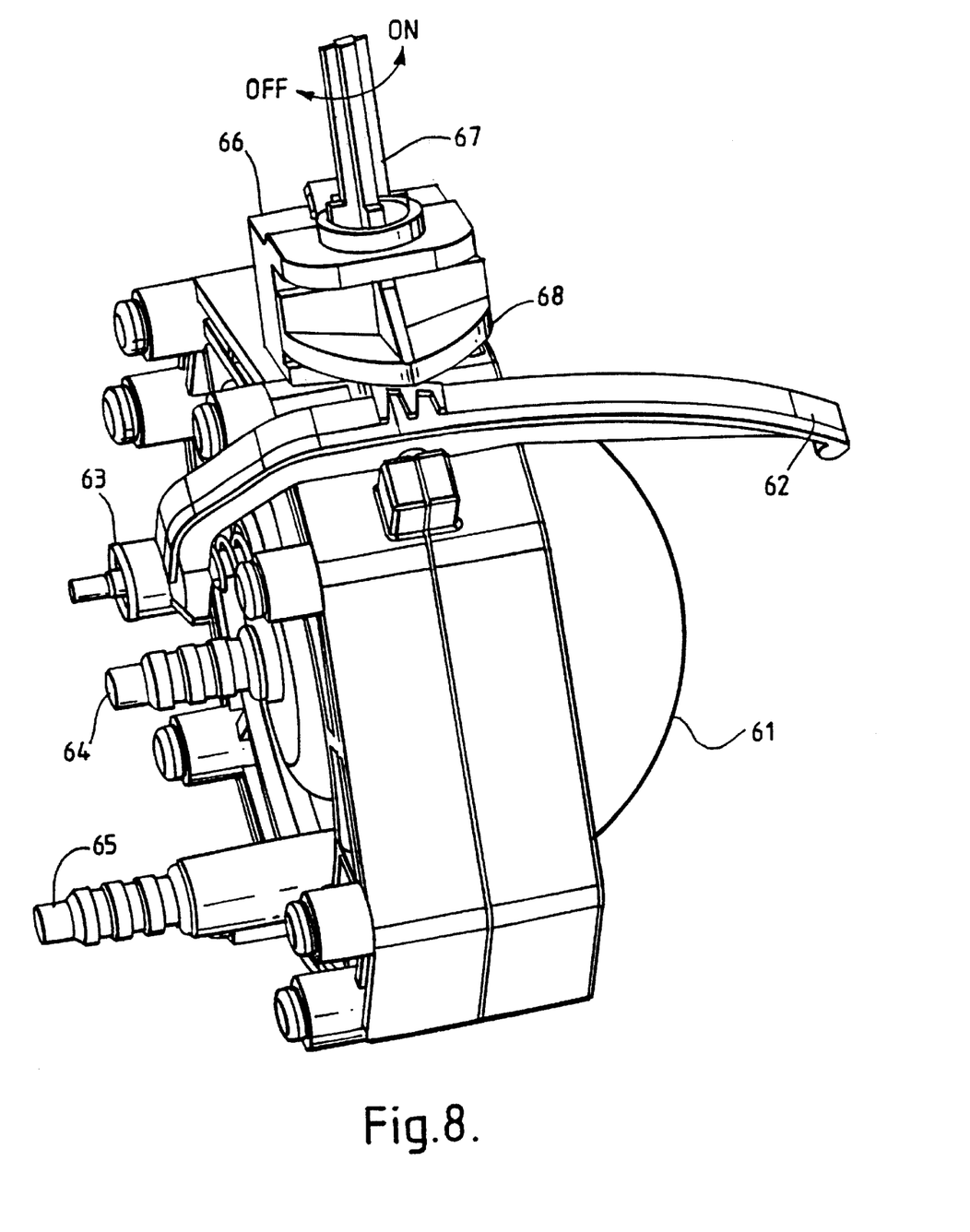
FIG. 8 shows an air accumulator within the air supply.

Referring to FIG. 8, the accumulator is shown which has a vent 63, thereby limiting the maximum expansion of the accumulator. As each pulse is delivered to the nebulizer, the diameter of the accumulator is reduced, and the vent 63 is closed.

The compressor may be mains powered or battery powered. The pump, especially a mains powered pump, operates continually during use, and operates to inflate the accumulator. When the pressure in the accumulator reaches the required level, a pressure switch in the hand-held part of the nebulizer is activated as is described in an earlier Patent application referred above. That switches the nebulizer ON. Once the treatment has been completed, the compressor is switched OFF. The accumulator deflates and the pressure switch in the hand-held part of the nebulizer deactivates the unit.

Referring to FIG. 8, the pump supplies air to the accumulator via a port 64. Inflation of the diaphragm 61 of the accumulator is controlled by an assembly including an arm 62 which is connected to a vent valve 63. When the diaphragm 61 of the accumulator reaches the maximum desired extension, it contacts the arm 62 to open the vent valve 63. This releases to atmosphere the flow of air from the compressor, and maintains the accumulator at a fixed extension. During use, air is removed from the accumulator via port 65 and the diaphragm 61 shrinks and loses contact with the vent arm 62 which closes the valve 63 allowing the compressor to recharge the accumulator until the vent arm 62 again operates the vent valve 63.

It is also advantageous to vent the accumulator to atmosphere when the compressor is switched off, and this is achieved by mounting the main power switch 66 on top of the accumulator with a rotary knob 67. The bottom of the knob 67 includes a cam 68 which contacts the vent arm 62 to open the vent 63 thereby releasing pressure from the accumulator. Simultaneously, the compressor is switched off. When the compressor is switched back on again, the cam 68 is disengaged from the vent arm 62, thereby closing the vent valve 63.

Figure 9:
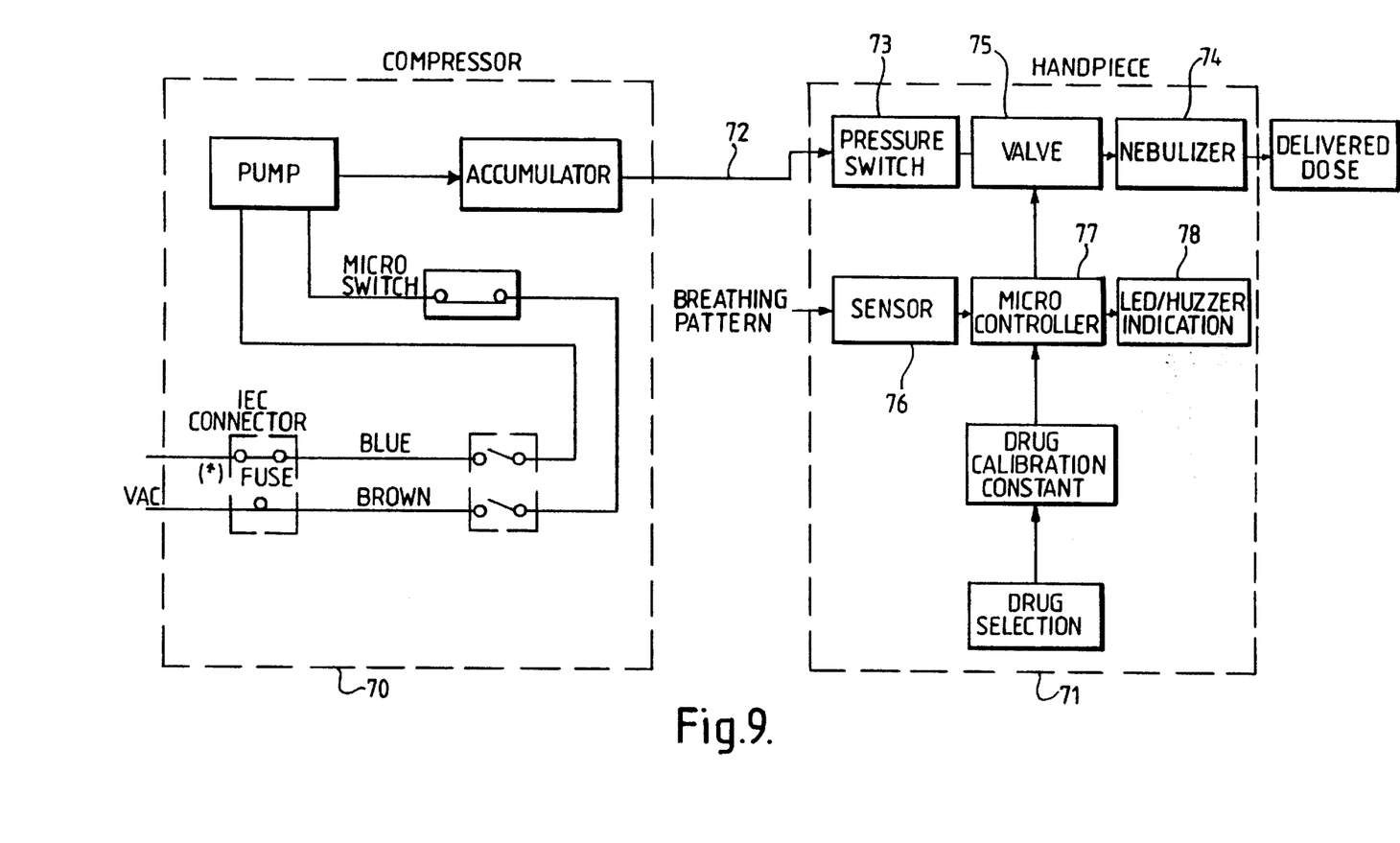
FIG. 9 is a schematic drawing showing the way in which the nebulizer is controlled.

FIG. 9 illustrates a simplified form of the way in which all of the components of the nebulizer are connected together. The compressor and accumulator 70 are shown as being separate from the hand-held part of the nebulizer 71, but connected by a tube 72 carrying the pressurised air into the nebulizer 71. In the compressor and accumulator part 70, the pump is shown to supply the accumulator 70 with compressed air. In the nebulizer part 71, the nebulizer is switched on at the pressure switch 73 by the presence of pressurised air in tube 72. The nebulizing part 74 of the nebulizer is controlled by a valve or manifold 75 which controls the pulses of pressurised air. The breathing pattern of a patient is detected by a sensor 76 which delivers information regarding the breathing pattern to the micro-controller 77 which, in turn, controls the manifold 75. Once a dose of medication has been delivered, indication means, such as an LED or buzzer 78 is activated by the micro-controller to indicate to the patient that treatment is complete.

Figure 10:
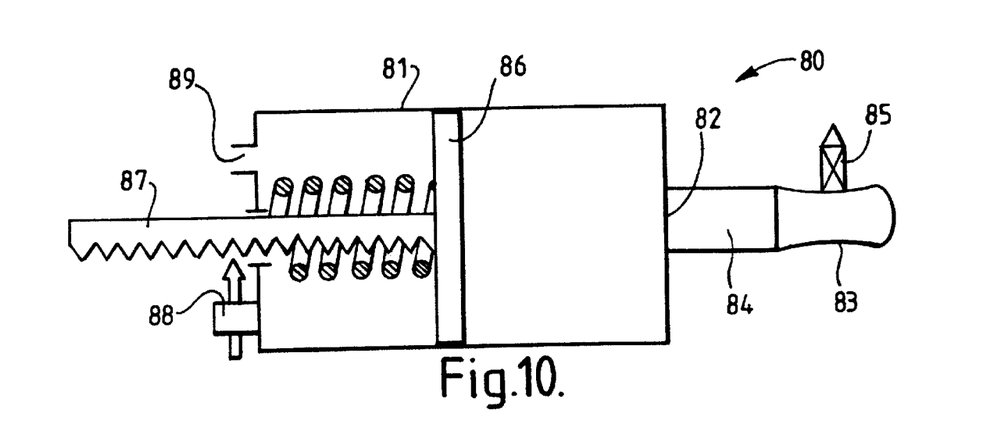
FIG. 10 is a schematic drawing of a dosimetric spacer according to the present invention.

A further embodiment of the invention is shown in FIG. 10 which is a dosimetric spacer 80 including a holding chamber 81 having a port 82 towards one end thereof to which is connected a mouthpiece 83. An air pressure sensor 84 is located between the mouthpiece 83 and holding chamber 81. This sensor 84 measures the pressure within the mouthpiece, from which the rate of flow of air inspired and exhaled by the patient can be measured air. The mouthpiece 83 also includes a vent 85 which allows a patient to exhale through the mouthpiece 83 without filling the holding chamber 81. More is disclosed on the vent below.

Within the holding chamber, a piston 86 is disclosed to move longitudinally to vary the volume of air available in the holding chamber 81 to a patient during inspiration. The piston includes a toothed connecting rod 87 which extends through the end of the holding chamber 81 such that the teeth may be engaged by the finger of solenoid 88. An air inlet 89 is located at the left hand end of the holding chamber in order to allow air to enter or leave the space behind the piston as the piston moves to the right or left.

In use, the piston 86 is pulled back so as to fill the holding chamber 81 with air. The air within the holding chamber 81 is then loaded with medication, either in the form of liquid droplets, or in the form of a cloud of powder. This is delivered into the holding chamber 81 through the port 82, and normally requires the removal of the mouthpiece 83 to do so. A mouthpiece 83 then can be replaced, and a patient breathes in and out through the mouthpiece 83. During inspiration, a patient inspires the medication-laden air from the holding chamber 81, and during exhalation, the exhaled air is vented to atmosphere by the vent 85. During exhalation, the solenoid 88 locks the connecting rod 87 of the piston 86 so that it will not move and so that the holding chamber will not fill with exhaled air. However, in accordance with the invention, the piston 86 is only free to move during a proportion of the inhalation phase, and it will be locked stationary by the. solenoid 88 during the inspiration by the patient of the end volume. Once the piston locks, the vent 85 is arranged such that the drop in pressure in the mouthpiece 83 caused by the locking of the piston 86 opens the vent 85 such that ambient air may be drawn into the mouthpiece. Of course, a separate vent might be included in the mouthpiece to carry out this function as appropriate.

The calculation of the pulse length during which the piston 86 is free to move to allow the dispensing of medication to the patient is determined in the same way as is described above in relation to the nebulizer. The inspiration of the patient during the previous three breaths is monitored by the sensor 84 such that the same calculations can be made as described above. On the subsequent breath, the sensor detects the commencement of a breath, and after the duration of the pulse, the piston is locked.

Such an arrangement reduces the waste of medication which is present in the end volume of the air normally breathed in by the patient.

This invention is applicable to other types of medical inhalers. For example, as described in the introduction to this specification, a dry powder inhaler is disclosed in U.S. Pat. No. 5,694,920 which uses a piezoelectric vibrator and an electrostatic charge plate to fluidize and disperse a dry powder into the air stream of the patient. The electrostatic charge plate can be operated in response to the patient's breathing pattern so as to produce pulses of the powder medication into the air stream leading to the patient. The length of the pulses can be determined in exactly the same way as in the embodiments previously described such that the dry powder is not dispersed into the end volume of the air stream leading to the patient. For the purposes of this description, the disclosure of the atomizer shown in U.S. Pat. No. 5,694,920 is incorporated by reference herein in its entirety as if set forth at length.

A further embodiment is shown in FIG. 11 together with an inhalation pattern shown in FIG. 12 which relates to the operation of the embodiment of FIG. 11. In that embodiment, a spacer 89 defines a holding chamber 90 which is arranged to be filled with medication-laden air from a nebulizer 91 which generates atomized medication directly into the holding chamber 90. The spacer 89 includes an outlet port 92 through which a patient will breathe via a mouthpiece (not shown). The patient will inhale medication-laden air from the holding chamber 90. On exhalation, expired air will be exhausted to the surroundings via an exhalation valve 93. The spacer 89 also includes an inhalation valve 94 which, during inhalation allows ambient air to enter the holding chamber 90 in order to allow the medication-laden air within the holding chamber to pass through the outlet port 92.

The spacer 89 also includes a sensor 95 which can detect when the holding chamber 90 has been filled with a specified concentration of airborne medication. For example, the sensor 95 might be a light obstruction or scattering sensor, an ultrasound or radio wave transmission time sensor or one which measures the electrical capacitance of the air.

Figure 11:
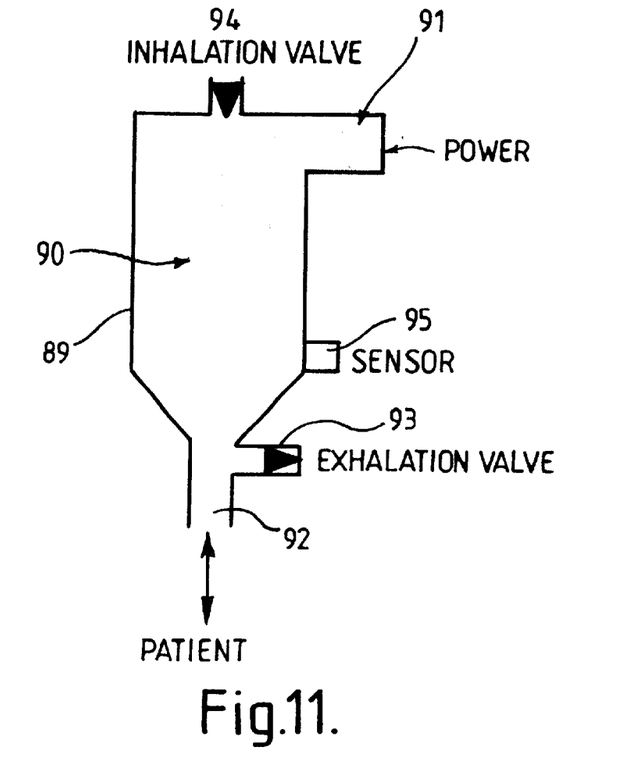
FIG. 11 is a schematic drawing of a further embodiment including a spacer and a nebulizer.

The embodiment shown in FIG. 11 reduces the patient treatment time by combining a spacer and a nebulizer. It increases the concentration of the aerosol "bolus" at the beginning of inhalation. The nebulizer 91 could be any one of a number of types of aerosol generation systems, typically either a gas-powered (pneumatic) nebulizer in which the nebulizer is powered by a stream of pressurized gas, or a mesh-type nebulizer. The patient breathes in and out via the outlet port 92 which would be connected to a mouthpiece (not shown). During inhalation, ambient air enters the holding chamber 90 via the inhalation valve 94, and during expiration, expired air is vented to atmosphere via the exhalation valve 93, bypassing the holding chamber 90.

Aerosolized medication is generated both during expiration and inspiration. The duration of the inhalation pulse has already been described. The duration of the expiration priming pulse depends on the method of nebulization and the volume of the spacer. For example, a gas-powered nebulizer operating at 6 litres per minute is sufficiently quick to fill, a holding chamber volume having a volume of 400 ml during expiration from a slow adult breathing pattern of about 10 breaths per minute at an inhalation to exhalation ratio of 1:2. A smaller volume chamber would be more practical for a wider range of patients, typically 100 to 300 ml which would take such a nebulizer a priming pulse of about 1 to 3 seconds to refill with aerosolized medication.

For a mesh-type nebulizer, the priming pulse would be limited to the maximum aerosol concentration that could be maintained in the spacer 89 without the droplets coalescing, which would result in a reduction in the respirable fraction and increase losses from sedimentation within the holding chamber 90. The aerosol concentration might typically be 0.1 to 1.0 mg per ml in the respirable range 1 to 5 microns. For a nebulizer with an output of 10 mg per second, and a spacer of 300 ml, the maximum priming pulse time would be 3.6 seconds. For any type of nebulizer, the priming pulse time could be limited by the use of the sensor 95 which detects when the holding chamber is filled with aerosolized medication to a specified concentration. Various types of sensors can be used, as described above.

Figure 12:
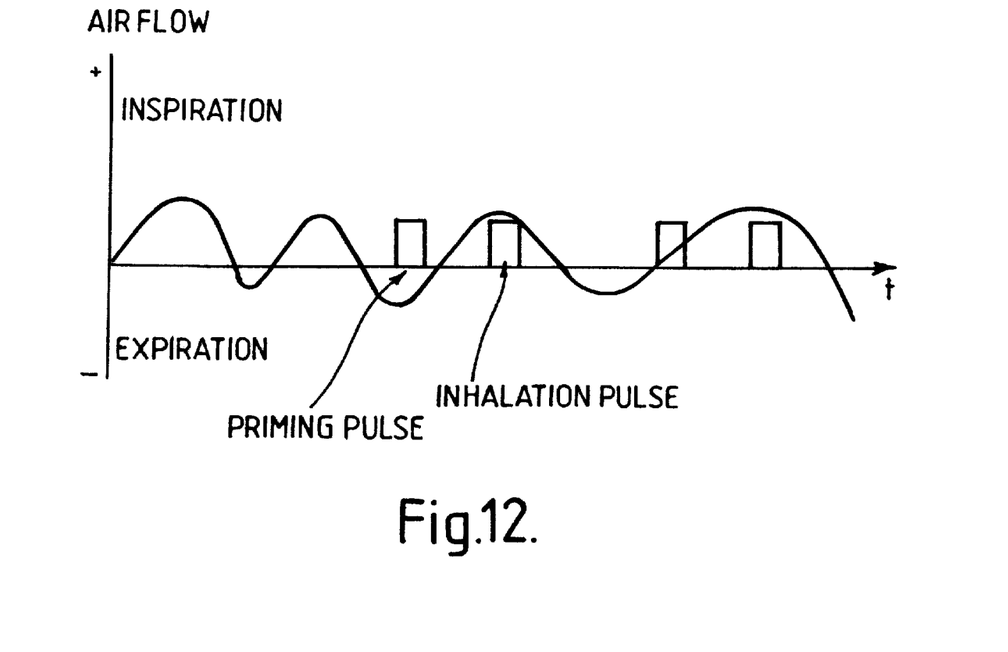
FIG. 12 is a graph showing the relationship between the priming pulse, the inhalation pulse and the breathing pattern of a patient using the embodiment shown in FIG. 11.

The occurrence of the priming pulse and the inhalation pulse with regard to time are shown in FIG. 12.

One or more embodiments of the present invention have been described. Nevertheless, it will be understood that various modifications may be made without departing from the spirit and scope of the invention. Accordingly, other embodiments are within the scope of the following claims.

What is claimed is:

1. A drug delivery apparatus comprising:
   a) a drug delivery device for selectively delivering both medication-laden air and non-medicated air to a patient for inspiration, wherein the medication-laden air is selected to be delivered in pulses;
   b) a sensor for monitoring a patient's breathing pattern; and
   c) a controller for controlling the drug delivery device to deliver the medication in pulses;
   wherein the length of the pulses and the proportion of time of the inspiratory phase of the breathing pattern during which the pulse is delivered are varied by the controller depending on the breathing pattern monitored by the sensor.

2. A drug delivery apparatus according to claim 1, wherein the apparatus is a nebulizer in which the drug delivery device is a device for atomizing a medication, and the controller controls the atomizing device to atomize the medication in pulses.

3. A nebulizer according to claim 2, wherein the controller which determines the duration of the pulse of atomization includes a tidal volume measuring device for measuring the tidal volume of a patient, a timer for measuring the duration of inspiration, an estimate storage device for storing an estimate of the volume of a patient's upper airway, and a pulse length calculator for calculating the duration of the pulse on the basis of the tidal volume measured by the tidal volume measuring device, the duration of inspiration measured by the timer, and the stored estimated volume of a patient's upper airway from the storage device.

4. A nebulizer according to claim 3, wherein the tidal volume measuring device includes a peak flow detector for measuring a patient's peak flow, and a tidal volume predictor for calculating the tidal volume on the basis of the peak flow measured by the peak flow detector, and the duration of inspiration measured by the timer.

5. A nebulizer according to claim 3, wherein the duration of the pulse is calculated on the basis of mean values of measured tidal volume and measured duration of inspiration derived from a number of earlier measurements of the breathing pattern of the patient.

6. A nebulizer according to of claim 2, further comprising a source of pressurised gas for atomizing the medication, the source including an accumulator for accumulating the gas under pressure, and a pulse limiter for limiting the duration of the pulse so as to maintain the accumulator in a state where it is always under some pressure.

7. A nebulizer according to claim 6, wherein the accumulator includes a valve which, when the accumulator is full, vents gas to atmosphere.

8. A drug delivery apparatus according to claim 1, wherein the apparatus is a spacer in which the delivery device for selectively delivering medication-laden air is a container defining a holding chamber for holding medication-laden air.

9. A drug delivery apparatus according to claim 8, wherein the controller, which determines the duration of the pulse, includes a tidal volume measuring device for measuring the tidal volume of a patient, a timer for measuring the duration of inspiration, an estimate storage device for storing an estimate of the volume of a patient's upper airway, and a pulse length calculator for calculating the duration of the pulse on the basis of the tidal volume measured by the tidal volume measuring device, the duration of inspiration measured by the timer, and the stored estimated volume of a patient's upper airway from the storage device.

10. A drug delivery apparatus according to claim 9, wherein the tidal volume measuring device includes a peak flow detector for measuring a patient's peak flow, and a tidal volume predictor for calculating the tidal volume on the basis of the peak flow measured by the peak flow detector, and the duration of inspiration measured by the timer.

11. A drug delivery apparatus according to claim 9, wherein the duration of the pulse is calculated on the basis of mean values of measured tidal volume and measured duration of inspiration derived from a number of earlier measurements of the breathing pattern of the patient.

12. A drug delivery apparatus according to claim 8, wherein the container defining the holding chamber includes at least one wall which is adjustable to reduce the volume of medication-laden air in the holding chamber to permit the medication-laden air to be delivered to a patient.

13. A drug delivery apparatus according to claim 8, wherein the container defining the holding chamber includes a piston moveable within the holding chamber to reduce the volume of medication-laden air in the holding chamber to permit the medication-laden air to be delivered to a patient.

14. A drug delivery apparatus according to claim 13, further comprising a piston controller for controlling the movement of the piston to deliver medication-laden air in pulses.

15. A drug delivery apparatus according to claim 8, further comprising a vent which allows inspiration of ambient air not laden with medication outside of the time in which a pulse is present.

16. A drug delivery apparatus according to claim 1, wherein the drug delivery device includes:
   a spacer defining a holding chamber; and
   a nebulizer for atomizing the medication into the holding chamber;
   wherein the controller controls the atomizer to atomize the medication in pulses.

17. A drug delivery apparatus according to claim 16, wherein the spacer includes an inhalation valve through which air enters the holding chamber to replace air inhaled from the holding chamber.

18. A drug delivery apparatus according to claim 16, further comprising a sensor arranged to detect the concentration of atomized medication within the holding chamber.

19. A nebulizer comprising apparatus for determining the duration of a pulse of atomization during inspiration, the apparatus including a tidal volume measuring device for measuring the tidal volume of a patient, a timer for measuring the duration of inspiration, an estimate storage device for storing an estimate of the volume of a patient's upper airway, and a calculator for calculating the duration of the pulse on the basis of the tidal volume measured by the tidal volume measuring device, the duration of inspiration measured by the timer, and the stored estimated volume of a patient's upper airway from the storage device.

20. A nebulizer according to claim 19, wherein the tidal volume measuring device includes a peak flow detector for measuring a patient's peak flow, and a tidal volume predictor for calculating the tidal volume on the basis of the peak flow measured by the peak flow detector, and the duration of inspiration measured by the timer.

21. A nebulizer according to claim 19, wherein the duration of the pulse is calculated on the basis of mean values of measured tidal volume and measured duration of inspiration derived from a number of earlier measurements of the breathing pattern of the patient.

22. A nebulizer according to claim 19, further comprising a container which defines a holding chamber, the container including at least one wall which is adjustable to reduce a volume of medicated air in the holding chamber to permit the medicated air to be delivered to a patient.

23. A nebulizer according to claim 19, wherein the container defining the holding chamber includes a piston moveable within the holding chamber to reduce a volume of medication-laden air in the holding chamber to permit the medication-laden air to be delivered to a patient.

24. A nebulizer according to claim 23, further comprising a piston controller for controlling the movement of the piston to deliver medication-laden air in pulses.

25. A nebulize according to claim 19, further comprising a vent which allows inspiration of ambient air not laden with medication outside of the time in which a pulse is present.

26. A nebulizer comprising:
   an atomizing device for atomizing a medication;
   a sensor for monitoring a patient's breathing pattern; and
   a controller for controlling the atomizing device to atomize the medication in pulses, wherein the length of the pulses and the proportion of time of the inspiration phase of the breathing pattern during which the pulse is delivered are varied by the controller depending on the breathing pattern monitoring by the sensor.

27. A method for determining the duration of a pulse during which medicated air is delivered to a patient during inspiration, comprising:
   (i) measuring the tidal volume of a patient;
   (ii) measuring the duration of inspiration of a patient;
   (iii) storing an estimate of the volume of a patient's upper airway; and
   (iv) calculating the duration of the pulse on the basis of the measured tidal volume of the patient, the measured duration of the inspiration and the stored estimated volume of the patient's upper airway.

28. A method according to claim 27, wherein the measurement of the tidal volume of a patient comprises:
   (v) measuring the peak flow of a patient; and
   (vi) predicting the patient's tidal volume on the basis of the measured peak flow and the measured duration of inspiration.

29. A method according to claim 27, wherein calculations are carried out on mean values derived from a number of earlier measurements of the breathing pattern of the patient.

30. A method according to claim 27, in which the pulse is a pulse of atomization of a medication whereby medication-laden air is delivered to a patient.

31. Drug delivery apparatus comprising a tidal volume predictor for predicting the tidal volume of a patient, including a detector for measuring a patient's peak flow, a timer for measuring the duration of inspiration, and a tidal volume calculator for calculating the tidal volume on the basis of the peak flow from the peak flow detector, and the duration of inspiration measured by the timer.

32. An apparatus according to claim 31, wherein the tidal volume is calculated on the basis of mean values of measured peak flow and measured duration of inspiration derived from a number of earlier measurements of the breathing pattern of the patient.

33. Apparatus according to claim 31, wherein the apparatus is a nebulizer.

34. A method of predicting the tidal volume of a patient comprising:
   (i) measuring a patient's peak flow;
   (ii) measuring the duration of inspiration of a patient;
   (iii) calculating the tidal volume on the basis of the measured peak flow and the measured duration of inspiration of the patient.

35. A method according to claim 34, wherein calculations are carried out on mean values derived from a number of earlier measurements of the breathing pattern of the patient.

* * * * *